United States Patent
Sundal et al.

(10) Patent No.: US 10,534,094 B2
(45) Date of Patent: Jan. 14, 2020

(54) GAS SENSOR (71) Applicant: Corentium AS, Oslo (NO)

(72) Inventors: Bjorn Magne Sundal, Oslo (NO); Erlend Bolle, Oslo (NO); Koki Yoshioka, Oslo (NO)

(73) Assignee: Airthings AS, Oslo (NO)

( * ) Notice: Subject to any disclaimer, the term of this patent is extended or adjusted under 35 U.S.C. 154(b) by 375 days.

(21) Appl. No.: 15/154,851

(22) Filed: May 13, 2016

(65) Prior Publication Data

US 2016/0299235 A1 Oct. 13, 2016

Related U.S. Application Data (63) Continuation of application No. 14/233,683, filed as application No. PCT/GB2012/051732 on Jul. 19, 2012, now Pat. No. 9,354,214.

(30) Foreign Application Priority Data

Jul. 20, 2011 (GB) .................................. 1112477.3

(51) Int. Cl.
*G01N 33/00* (2006.01)
*G01T 1/178* (2006.01)
*G01T 7/00* (2006.01)

(52) U.S. Cl.
CPC .......... *G01T 1/178* (2013.01); *G01N 33/0009* (2013.01); *G01T 7/00* (2013.01); *Y10T 29/49826* (2015.01)

(58) Field of Classification Search
CPC ....... G01T 1/178; G01T 7/00; G01N 33/0009; H05K 9/0022
See application file for complete search history.

(56) References Cited

U.S. PATENT DOCUMENTS 4,518,860 A 5/1985 Alter et al.
4,778,992 A 10/1988 Wheeler
(Continued)

FOREIGN PATENT DOCUMENTS

EP 0 108 956 A1 5/1984
EP 0 280 416 A1 8/1988
(Continued)

OTHER PUBLICATIONS

Calamosca et al., "The features of the new radon gas CR-39 dosemeter developed at the ENEA Institute of Radioprotection," ENEA-ION-IRP, Montecuccolino, V. dei Colli 16, 40136 Bologna, Italy, Radiation Measurements, vol. 36, Jun. 1, 2003, pp. 221-224.
(Continued)

*Primary Examiner* — Blake A Tankersley
(74) *Attorney, Agent, or Firm* — Klarquist Sparkman, LLP (57) ABSTRACT

A gas sensor instrument comprises a housing formed of two parts (102, 10) and a diffusion chamber inside the housing. The diffusion chamber is formed from two parts (106, 108) and at least one of the diffusion chamber parts is formed integrally with one of the housing parts. This allows a reduction in size of the instrument without compromising the size of the diffusion chamber. Additionally, a tubular projection is formed integrally with one of the housing parts to form part of a Faraday cage for shielding an amplifier circuit of the instrument.

7 Claims, 8 Drawing Sheets

(56) References Cited

U.S. PATENT DOCUMENTS

| | | | |
|---|---|---|---|
| 4,859,865 | A | 8/1989 | Vandenburgh |
| 4,948,970 | A | 8/1990 | Port et al. |
| 4,992,658 | A | 2/1991 | Ramsey, Jr. et al. |
| 5,068,538 | A | 11/1991 | Harley |
| 5,132,535 | A | 7/1992 | Steck |
| 5,150,282 | A * | 9/1992 | Tomura ............... H04B 1/3833 174/367 |
| 5,489,780 | A * | 2/1996 | Diamondis ............ G01N 23/00 250/253 |
| 6,157,546 | A * | 12/2000 | Petty .................... H05K 9/0032 174/379 |
| 8,143,584 | B2 | 3/2012 | Burke et al. |
| 2004/0232345 | A1 | 11/2004 | Jagam et al. |
| 2007/0291464 | A1 | 12/2007 | Wang |
| 2009/0230305 | A1 | 9/2009 | Burke et al. |
| 2009/0306524 | A1* | 12/2009 | Muhlsteff ............... A61B 5/021 600/485 |
| 2009/0310317 | A1* | 12/2009 | Horten ................ H05K 9/0022 361/752 |
| 2010/0177498 | A1 | 7/2010 | Choi et al. |
| 2012/0034959 | A1* | 2/2012 | Edeler .................. H04M 1/035 455/575.5 |

FOREIGN PATENT DOCUMENTS

| | | |
|---|---|---|
| EP | 1 148 774 A1 | 10/2001 |
| GB | 2 476 123 A | 6/2011 |
| WO | WO 98/47340 | 10/1998 |
| WO | WO 99/26053 | 5/1999 |
| WO | WO 2005/004711 A1 | 1/2005 |
| WO | WO 2008/080753 A1 | 7/2008 |

OTHER PUBLICATIONS

International Search Report for PCT/GB2012/051732, dated Apr. 17, 2013, 8 pages.

Koo et al., "Sensitivity of LR115 detector in diffusion chamber to 222 Rn in the presence of 220Rn," Applied Radiation and Isotopes 56, Jul. 2002, pp. 953-956.

Search Report from GB Patent Office, for GB1112477.3, dated Nov. 18, 2011, 3 pages.

Search Report from GB Patent Office, for GB1112477.3, dated Nov. 18, 2011, 4 pages.

* cited by examiner

GAS SENSOR

CROSS REFERENCE TO RELATED APPLICATIONS

This is a continuation of U.S. application Ser. No. 14/233,683, filed Jan. 17, 2014, which is the U.S. National Stage of International application No. PCT/GB2012/051732, filed Jul. 19, 2012, which was published in English under PCT Article 21(2), which in turn claims the benefit of GB 1112477.3, filed Jul. 20, 2011, all of which are hereby incorporated herein by reference.

The present invention relates to gas sensors. Preferred embodiments relate to radon gas sensors.

Radon is a radioactive element which at normal temperature and pressure is a gas. It is colourless, odourless and tasteless which means that its presence and concentration is not readily detectable by human beings. However, due to its radioactivity, it can be harmful if the concentration is too high. At normal concentrations, radiation from radon typically accounts for around half of a person's annual natural radiation dose.

The most stable isotope of radon is radon-222 which has a half life of 3.8 days and is produced as part of the decay chain of uranium-238 which is present throughout the Earth's crust. Being a noble gas, radon readily diffuses out of the ground and into the air around us. The daughter products of radon decay tend to be charged particles which will readily stick to dust or smoke particles in the air. When these particles are inhaled, they can lodge in the lungs and the subsequent radiation from decay of the radon daughter products causes a risk of lung cancer. Consequently, higher concentrations of radon lead to higher risks of cancer.

The concentration of radon in the atmosphere depends, amongst other things, on ventilation. Areas with good ventilation will have lower radon concentrations, whereas a lack of ventilation leads to radon accumulation and thus increases the radiation level in such areas. Radon levels outside therefore tend to be lower than inside buildings. For example, typical radiation doses from radon may be around 10-20 $Bq/m^3$ outside and may be around 100 $Bq/m^3$ inside. Radon levels can also vary significantly due to variations in geographic location (e.g. different geologies), or due to differences in building materials.

Radon decays by emission of an alpha particle with an energy of 5.5 MeV. The resultant Polonium-218 has a half life of about 3 minutes before emitting an alpha particle of 6.0 MeV. The resultant Lead-214 has a half life of around 27 minutes before beta-decaying to Bismuth-214 which in turn has a half life of 20 minutes and beta-decays to Polonium-214. Polonium-214 has a half life of about 164 microseconds before emitting an alpha particle of 7.7 MeV resulting in Lead-210 which has a half life of 22 years and is thus relatively stable.

Detection of radon to date has been divided into two main methods. The first method is active detection of alpha particles using a photodiode and the second method is passive detection of alpha particles using a track detector. Typically the first method requires a large instrument and needs electrical power to be supplied. Such instruments have typically only been used for larger scale, e.g. commercial or industrial measurements as the instruments are more bulky and expensive. The photodiode is placed in a diffusion chamber of the device. Alpha particles hitting the photodiode create a number of electron-hole pairs which will cause a small current to be generated. These current signals can be detected and counted to provide a measure of the radon concentration within the diffusion chamber. Such active measurements can be provided continuously in time rather than having to wait for the results of a laboratory analysis.

The second method uses much smaller detectors with no power requirement and is thus much more suited to domestic customers. A passive (i.e. unpowered) track chamber is typically placed in a selected location and left for a predetermined period of time (typically from a few weeks and up to about 3 months) after which it is sent back to a lab for analysis. Alpha particles emitted within the chamber leave tracks on a film which is also disposed within the chamber. These tracks can be detected in the lab and counted thus providing a measure of the radon concentration in the air within the chamber.

WO 2008/080753 describes a passive radon detector device with a diffusion chamber rotatably mounted above the detector so that it can be rotated in and out of the "ON" position above the detector. When the chamber is in position above the detector, the detector will detect alpha particles from gas which diffuses into the chamber. When the chamber is rotated out of position (the "OFF" position), the detector is covered (the chamber volume is essentially reduced to zero) and is therefore effectively isolated from radon in the surrounding environment.

US 2009/0230305 describes an active radon detector device which is battery powered. The photodiode detector is mounted on the main PCB and is covered by a sampling chamber, also mounted on the main PCB. Air enters and leaves the sampling chamber through apertures in the PCB. These apertures are optionally covered by a filter to exclude undesired debris such as smoke, dust, and the like.

U.S. Pat. No. 5,489,780 describes another active radon detector device in which a pressed metal filter is used as the wall of the diffusion chamber. This filter is mounted directly on the PCB over the photodiode detector, thus defining the sampling volume.

According to the present invention there is provided a gas sensor instrument, comprising: first and second housing parts which mate together to form an instrument housing; and first and second diffusion chamber parts which mate together to form a diffusion chamber; wherein at least one of the first and second diffusion chamber parts is integrally formed with at least one of the first and second housing parts.

By integrally forming the diffusion chamber with at least one of the housing parts, the number of components of the instrument is reduced. Also, such integral formation allows the diffusion chamber volume to extend fully to the inner surface of the integral housing part. Thus the size of the instrument can be minimized without compromising the diffusion chamber size. The instrument housing defines a first volume and the diffusion chamber defines a second, smaller volume within the first volume. With the integral formation, the instrument housing part simultaneously forms a boundary surface of both the first and second volumes.

Although one diffusion chamber part could still be formed as a separate component, preferably both diffusion chamber parts are integrally formed with the housing parts, i.e. one chamber part on each housing part. This provides the same benefits at both ends of the diffusion chamber, thus providing the optimum instrument thickness for a given height of diffusion chamber. Preferably therefore, the first diffusion chamber part is integrally formed with the first housing part and the second diffusion chamber part is integrally formed with the second housing part.

The two chamber parts could simply meet in an abutting relationship with diffusion of gas into the chamber occurring along the abutted join. However the diffusion path length for such an arrangement may not provide sufficient capability to exclude certain particles diffusing into the diffusion chamber. For example, in the case of radon gas, such an arrangement would not sufficiently prevent radon daughter products from diffusing into the diffusion chamber. Ideally, the radiation detected within the diffusion chamber should correlate with the concentration of radon gas within the diffusion chamber, but such measurements are skewed if a radon decay chain can begin outside the chamber, with the daughter product then diffusing into the chamber where subsequent decays can then be detected within the chamber.

In preferred embodiments therefore, one of the first and second diffusion chamber parts is an inner diffusion chamber part and the other is an outer diffusion chamber part, and the first and second diffusion chamber parts overlap with each other such that a perimeter wall of the inner part is disposed inside a perimeter wall of the outer part.

This arrangement allows different particles to be separated according to the diffusion path length created by the overlap. The overlap region is preferably sized so as to allow diffusion of the gas to be monitored into the diffusion chamber, while excluding undesired particles. For example, in the case of radon gas, once a radon-222 atom has decayed, the rest of the decay chain through to the relatively stable lead-210 isotope is typically less than an hour. Creating a diffusion path length with a diffusion time constant greater than that time will greatly reduce the probability of the detector picking up data which corresponds to radon decays outside of the diffusion chamber. In fact, the diffusion path can be designed to have a diffusion time constant less than an hour as the radon daughters are all metallic and tend to stick to surfaces, so the movement of daughters is not governed by diffusion alone and the daughters therefore do not progress along the diffusion path so easily. The diffusion time constant of the diffusion path is preferably greater than 30 minutes, i.e. greater than about 50% of the expected combined lifetime of the daughter products.

The overlap distance, and hence the diffusion path length, can readily be selected by the skilled person according to the properties of the particles that are to be allowed to diffuse through and the properties of those that are not. In some preferred embodiments, the overlap may be greater than 5 mm, preferably in the range of 5-15 mm. In other preferred embodiments, the diffusion path length is at least 15 mm. Although such a long path is more than adequate to exclude radon daughters from the diffusion chamber, it is not so long that it restricts radon itself reaching the interior of the chamber. This distance is measured in the mating direction of the two diffusion chamber parts, e.g. when the two parts are mated together, the outer diffusion chamber part may overlap the inner diffusion chamber part by 15 mm.

In preferred embodiments, the first and second diffusion chamber parts are each formed as a tube, open at one end and closed at the other. A first printed circuit board may be disposed within the diffusion chamber and the first printed circuit board is then clamped between the open end of one diffusion chamber part and the closed end of the other diffusion chamber part.

In other words, the diffusion chamber parts are preferably each formed as a perimeter wall extending out from the respective housing part to form a cup-shape. The rim of the wall of the smaller diffusion chamber part presses against the printed circuit board which in turn is pressed against the bottom of the cup-shape of the larger diffusion chamber part (which is preferably the inner surface of the housing part). The printed circuit board is thus held in place by being sandwiched between the two diffusion chamber parts. This arrangement removes the need for any additional fixing means to hold the printed circuit board in place. Therefore no adhesive or screws or the like are required to attach the printed circuit board to either of the instrument housing parts. This reduces both the number of components in the device and the time required for assembly. Both of these factors reduce the overall cost of producing the instrument.

As particles must be allowed to diffuse into the diffusion chamber, the inner diffusion chamber part must not seal against the printed circuit board. Preferably therefore the first and second diffusion chamber parts are each formed as a tube, open at one end and closed at the other, and the inner diffusion chamber part comprises one or more spacer projections on a rim thereof to ensure a minimum gap adjacent the rim. The size of the projections determines the size of the gap and thus affects the diffusion rate across the diffusion path. Preferably therefore the size of the projections is selected according to the principles discussed above for discriminating which particles can diffuse into or out of the chamber.

Similarly, one of the first and second diffusion chamber parts may be provided with one or more spacers in the overlap region to ensure a minimum separation between the two chamber parts. Such spacers define the width of the diffusion path formed between the inner and outer diffusion chamber parts and the size can likewise be selected to discriminate which particles can diffuse into or out of the chamber. These lateral spacers (as opposed to the rim spacers) may be formed as simple projections, but are preferably formed as ribs extending in the mating direction along the wall of the diffusion chamber part. It will be appreciated that these spacers could be formed in either the inner surface of the wall of the outer chamber part or on the outer surface of the wall of the inner chamber part. The spacers could be formed on both diffusion chamber parts, although for simplicity are preferably formed on only one part.

The lateral spacers and the rim spacers described above could be separate elements, but are preferably integrally formed with the diffusion chamber parts for simplicity.

A consequence of the arrangement of this invention is that the diffusion chamber is not situated on the main printed circuit board for the processing circuitry. Therefore the actual sensor for the instrument, which is located inside the diffusion chamber is separated from the main printed circuit board with the processing circuitry. An electrical connection must therefore be provided between the detector inside the diffusion chamber and the processing circuitry outside the diffusion chamber. An electrical conductor could simply be passed through the overlap region, following the same path as is taken by the diffusing particles. However the small dimensions of the diffusion path mean that the conductor would tend to be squashed and stretched during the mating process with likely consequential damage to the conductor. Alternatively, if the conductor were too thick, the diffusion path would be widened and the diffusion time constant for that path could be adversely reduced.

Preferably therefore one of the first and second diffusion chamber parts is provided with a channel for accommodating an electrical conductor passing through the overlap region from the inside to the outside of the chamber.

It will be appreciated that different types of conductor may be used according to the circumstances, and indeed more than one such conductor could be used, optionally with more than one channel. However in a preferred embodiment a coaxial cable is used so as to maintain shielding of the detector signal after it leaves the diffusion chamber.

The channel could be formed in either the inner diffusion chamber part or the outer diffusion chamber part, or it could be partly formed in both. However, if the walls of the diffusion chamber parts are thin then reinforcement might be needed in the region of the channel. It is desirable not to provide any structure on the inside of the diffusion chamber which would reduce the volume of the chamber and therefore preferably the channel is formed in the outer diffusion chamber part and the diffusion chamber wall has increased thickness in the region of the channel. The increased thickness provides the necessary strength for the wall in the region of the channel. The increased thickness is preferably provided only in the region where it is required so as to minimise weight and bulk of material.

The inner surfaces of the first and second housing parts may be electrically conductive. This may be achieved either by forming the housing parts from a conductive material, e.g. a conductive plastics material, or by coating the housing parts with a conductive layer, e.g. using a vapour deposition or plasma spraying technique. In preferred embodiments, the parts are coated using a vacuum metallization technique. When the two housing parts are mated together, they then come into electrical contact and form a Faraday shield around the interior of the instrument, thus shielding it from external sources of electromagnetic radiation. Additionally, the diffusion chamber parts which are integrally formed with the housing parts are also thus electrically conductive and form another Faraday cage around the diffusion chamber and thus around the detector. This is particularly advantageous as the detector is typically highly sensitive to electromagnetic radiation. For example in the case of radon measurements, a photodiode is often used. The photodiode is sensitive to light or other electromagnetic radiation and so it is highly beneficial to shield the detector in this way. By forming the diffusion chamber parts integrally with the housing parts, the shielding of the diffusion chamber both from sources external to the instrument and sources internal to the instrument (but external to the diffusion chamber) is achieved in a simple and efficient fashion.

Preferably the instrument further comprises a second printed circuit board outside the diffusion chamber, said second printed circuit board including an amplifier circuit, and preferably one of the first and second housing parts comprises an integral tubular projection extending from the inner surface thereof towards the second printed circuit board so as to surround the amplifier circuit, and wherein the inner surface and a rim of said integral tubular projection are electrically conductive so that the tubular projection forms part of a Faraday cage around the amplifier circuit.

As the signal from the detector is typically very weak, it is desirable to protect that signal from electromagnetic noise until it has been amplified. It is therefore desirable to shield at least the first amplifier stage in a similar manner to the detector. A traditional Faraday cage could simply be attached over the relevant circuit in known fashion. However, the above arrangement can use the electrically conductive housing part to provide the same function. Thus the shield can be formed integrally with the housing part in the same fashion as the diffusion chamber parts. This reduces the number of components as a separate Faraday cage is no longer required to be fitted to the PCB. This also removes a step from the PCB assembly process.

The second printed circuit board preferably comprises at least first and second conductive layers, the second conductive layer being located further from the tubular projection than the first conductive layer, the amplifier circuit is preferably formed on the first conductive layer, and preferably one or more electrically conductive vias through the second printed circuit board electrically connect the rim of the tubular projection with the second conductive layer.

The components of the processing circuitry are preferably all mounted on one layer of the printed circuit board. Mounting all components and all inter-component conductive tracks on one side of a printed circuit board simplifies the assembly process. For such circuits, it would not normally be necessary to use a PCB with a second conductive layer, but in this arrangement the second conductive layer forms the back of the Faraday cage for the amplifier circuit. The second layer is electrically connected to the tubular projection by a number of vias which are provided through the PCB. The vias may connect the first conductive layer to the second conductive layer and they may be linked by an exposed contact track on the first conductive layer which substantially surrounds the amplifier circuit and which provides an electrical contact for the tubular projection of the housing part, thus ensuring electrical connection of all parts of the Faraday cage. By "substantially surrounds" it is meant that the track does not completely surround the amplifier circuit, but rather leaves enough room for a conductive track to carry the output signal of the amplifier circuit to exit from within the Faraday cage. This break in the conductive track (and thus a hole in the Faraday cage) is kept as small as is practically possible so as not to impair the functioning of the cage. The contact track on the first conductive layer may simply be an exposed region of a larger area of the conductive layer which is preferably connected to the circuit ground.

The exit track (or tracks) from the amplifier circuit will typically be protected by an insulating covering, e.g. a solder stop. This ought to be sufficient to prevent short circuiting through contact with the conductive tubular projection which is pressed down around the amplifier circuit to form the Faraday cage. However if the solder stop is incomplete or becomes damaged, or if the pressure applied between the PCB and the tubular projection is high enough to rupture the solder stop, the exit track would be in electrical contact with the Faraday cage, leading to a faulty instrument. Therefore preferably the tubular projection includes a recess in the rim thereof which does not make contact with the second printed circuit board. The recess is located such that when the tubular projection is in position over the amplifier circuit, the recess is located above the exit track. This arrangement protects the exit track from short circuiting problems. This recess necessarily increases the size of the hole that is formed in the Faraday cage, but this can be kept to a size that does not significantly impair the functioning of the cage while still protecting the conductive tracks on the PCB.

The gas sensor instrument could be any gas sensor which requires a diffusion chamber. The diffusion chamber size and the diffusion path and the detector can be selected according to the particular function of the instrument. In preferred embodiments however, the gas sensor instrument is a radon gas sensor.

In preferred embodiments of a radon gas sensor, the diffusion chamber is cylindrical, preferably having a length of 15-25 mm and a radius of 10-25 mm. Such chambers have a volume ranging from about 5 to 50 cubic centimetres. The diffusion path length is preferably in the range of 5-15 mm and the diffusion path width (i.e. the smallest, most restrictive dimension of the path) is preferably in the range of 0.05 to 0.25 mm, most preferably about 0.1 mm. The above-described rib spacers and rim projections thus each preferably project 0.05 to 0.25 mm from their respective surfaces.

The invention also extends to a method of making a gas sensor instrument. Therefore according to a further aspect, the invention provides a method of making a gas sensor instrument comprising first and second housing parts and first and second diffusion chamber parts, wherein the first diffusion chamber part is integrally formed with the first housing part and the second diffusion chamber part is integrally formed with the second housing part and wherein the method comprises a step of simultaneously mating the first housing part with the second housing part and the first diffusion chamber part with the second diffusion chamber part.

The preferred features described above in relation to the apparatus are equally preferred features of the method of making the instrument.

The provision of part of a Faraday cage on an instrument housing is believed to be independently inventive. Therefore, according to another aspect, the invention provides an instrument comprising a housing and a printed circuit board disposed within the housing, and wherein a housing part of the instrument comprises an integral tubular projection extending from the inner surface thereof towards the printed circuit board so as to surround at least one electronic component thereon, wherein the inner surface and a rim of said integral tubular projection are electrically conductive so that the tubular projection forms part of a Faraday cage around said at least one component.

The advantages and preferred features of this invention are as described above. All features which are described above in relation to the first aspect can equally apply as preferred features of this aspect of the invention.

Accordingly, in preferred embodiments, the printed circuit board comprises at least first and second conductive layers, the second conductive layer being located further from the tubular projection than the first conductive layer, wherein the at least one component is mounted on the first conductive layer, and wherein one or more electrically conductive vias through the printed circuit board electrically connect the rim of the tubular projection with the second conductive layer. The tubular projection preferably includes a recess in the rim thereof which does not make contact with the printed circuit board.

A single via provides sufficient electrical connection between the rim and the second conductive layer (i.e. between the shield cover and the shield back plate). However a more consistent and reliable connection may be obtained by using a plurality of vias to form the connection. Preferably therefore a plurality of vias are positioned along a boundary which substantially surrounds the component. The boundary preferably follows the shape of the rim of the tubular projection, for the most part. The path of the boundary may deviate from the rim, e.g. in the region where the coaxial cable for the input signal enters the Faraday cage. A slit may be formed in the PCB for the signal cable to enter the Faraday cage. The rim of the upper shielding enclosure (i.e. the integral tubular projection) may lie directly across this slit, thereby enclosing the end of the cable within the Faraday cage. However the boundary (i.e. the vias) may be positioned (or the path may deviate) sufficiently far from the edge of the PCB that they are not interrupted by the slit.

The vias may simply provide an electrical connection of the tubular projection to the second layer. However, preferably the one or more vias electrically connect one or more portions of the first layer with the second layer. In a normal PCB design process, the unused portions of the first layer are often connected to the circuit ground. As the Faraday cage is preferably also connected to the circuit ground, there is no need to remove the first conductive layer in the contact region between the vias and the rim of the tubular projection. The contact region must however be exposed for electrical contact, so no solder stop should be applied over that region.

Preferably the second layer is substantially continuous across the area defined by the rim of the tubular projection. A continuous portion of the second layer has no holes or interruptions therein and thus provides a good shield against external electromagnetic radiation. "substantially continuous" means that any holes or interruptions in this region of the second layer are small enough that they do not significantly affect the shielding capabilities of the Faraday cage. It will be appreciated that this is dependent on the wavelengths to be blocked and will thus vary with application.

The component(s) to be shielded may be any components which are susceptible to electromagnetic interference or noise. However, in preferred embodiments the integral tubular projection surrounds a plurality of components forming a circuit, preferably an amplifier circuit.

It will be appreciated that the inside surface of the instrument housing could be conductive just on the inside surface of the tubular projection or just in the local region surrounding it. However, for manufacturing convenience, preferably the whole inside surface of the instrument housing is conductive. This may be achieved via use of conductive plastics material or via coating with a conductive material, e.g. by vacuum metallization, plasma spraying or other coating processes.

Preferably the instrument is a radon gas sensor.

The invention also extends to a method of shielding electronic components. Therefore according to a further aspect, the invention provides a method of shielding at least one electronic component on a printed circuit board disposed within an instrument housing, comprising: providing a housing part of the instrument with an integral tubular projection extending from the inner surface thereof; making the inner surface and a rim of said integral tubular projection electrically conductive; and engaging said integral tubular projection with said printed circuit board so as to surround said at least one electronic component such that the tubular projection forms part of a Faraday cage around said at least one component.

The preferred features discussed are equally applicable and are equally preferred features of the method.

Preferred embodiments of the invention will now be described, by way of example only, and with reference to the accompanying drawings in which.

Figure 3:
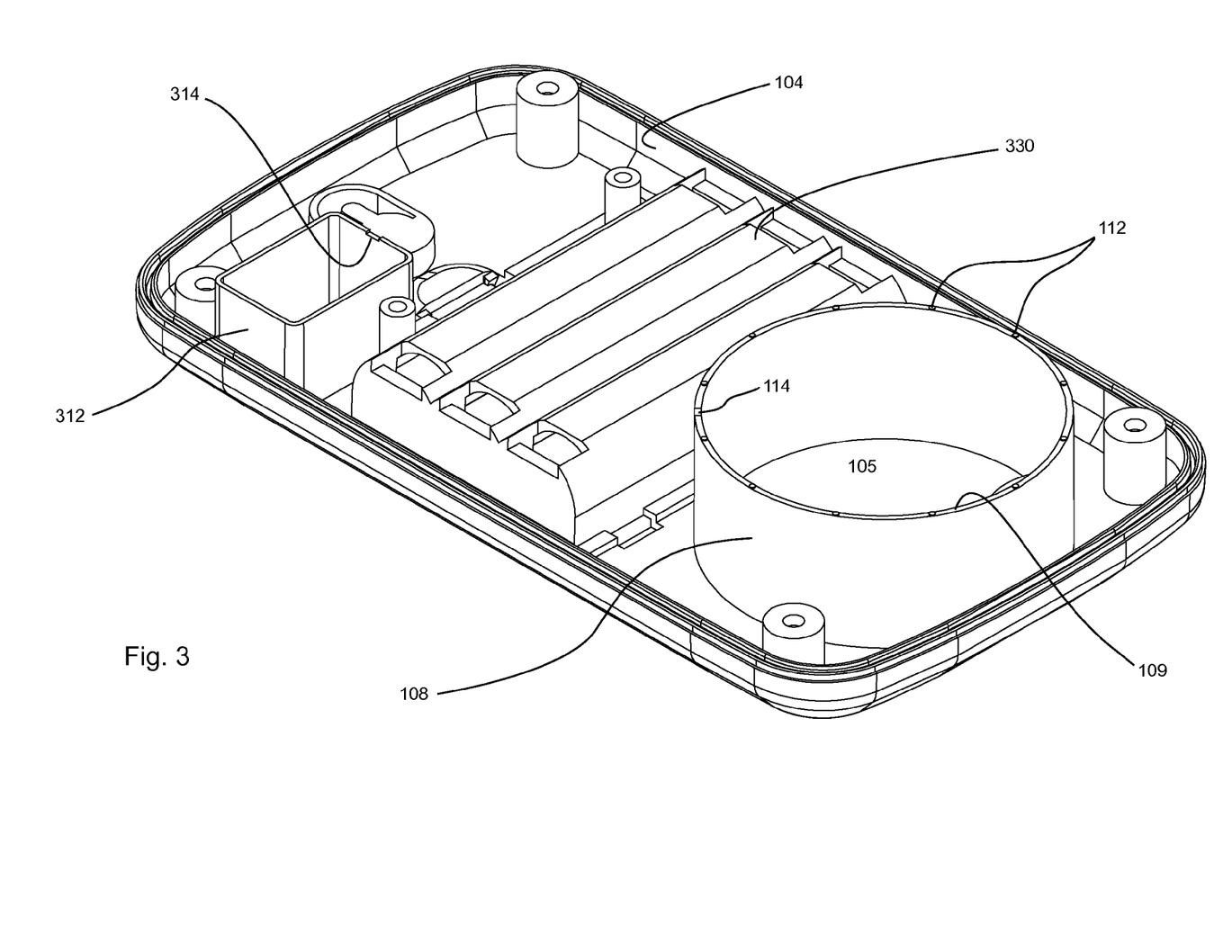
FIG. 3 shows a perspective view of a rear housing part of an embodiment of the invention.
Figure 6:
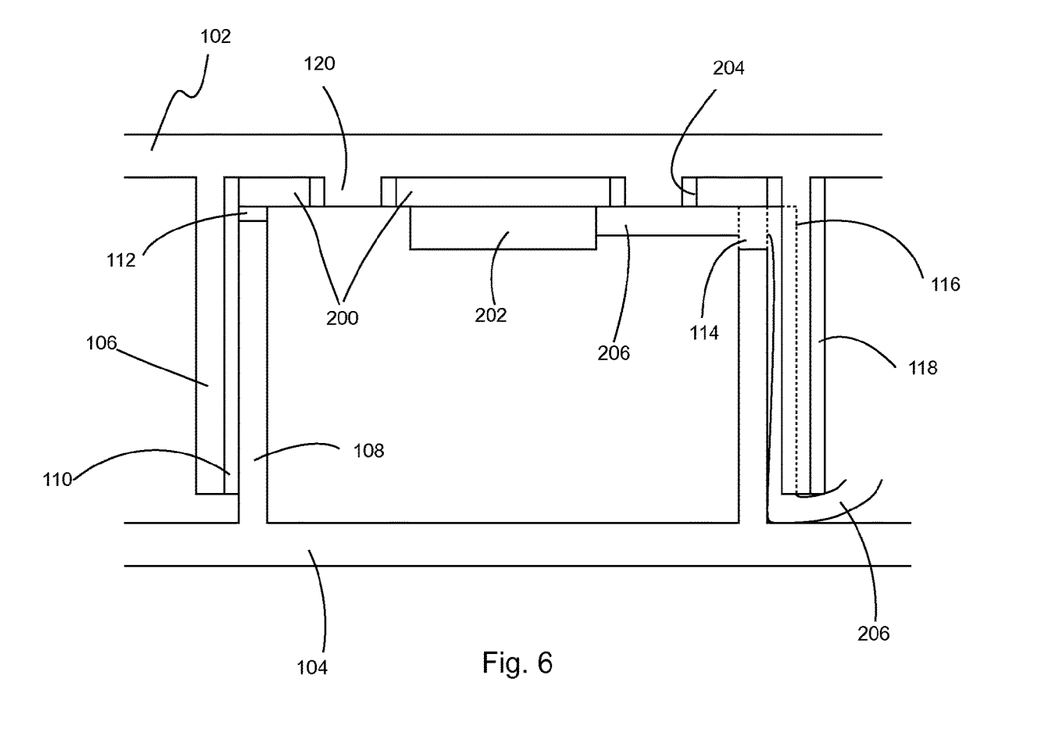
FIG. 6 shows a cross-sectional view of the diffusion chamber of an assembled instrument.

A radon gas sensor instrument 100 according to an embodiment of the invention comprises two housing parts—a front housing part 102 (shown in FIG. 1) and a rear housing part 104 (shown in FIG. 3). The instrument 100 has a diffusion chamber 105 which encompasses a well-defined volume of gas. A photodiode 202 is disposed within the diffusion chamber 105 for detecting alpha particles which are emitted within the diffusion chamber 105. Photodiode 202 is provided on a first PCB 200 at one end of the diffusion chamber 105. This arrangement is best illustrated in FIG. 6.

The diffusion chamber 105 is formed from a first chamber part 106 and a second chamber part 108. First chamber part 106 is formed integrally with the front housing part 102 and second chamber part 108 is formed integrally with the rear housing part 104. In this embodiment, each chamber part 106, 108 is formed from a circular perimeter wall which extends out from the front or rear face of the respective housing part 102, 104, thus forming a circular cylindrical tube 106, 108 which is closed at one end (the end at which it is integrally moulded with the housing part 102, 104) and open at the other end (i.e. open at the end which faces the opposite housing part 104, 102. Thus when the two chamber parts 106, 108 are brought together, they form a closed cylindrical diffusion chamber 105. It will be appreciated that in other embodiments the chamber need not by a circular cylinder, but may in fact be any appropriately chosen shape.

Forming the diffusion chamber parts 106, 108 integrally with the housing parts 102, 104 not only reduces the number of manufacturing steps involved in producing the instrument 100, but also allows the overall size of the instrument to be minimized without compromising the size of the diffusion chamber 105. In general, it is desirable not to reduce the volume of the diffusion chamber 105 as the larger volume will yield more decay events per unit time and therefore more accurate results. At the same time, it is desirable to reduce the size of the instrument 100 so as to reduce bulk, reduce material costs and make the unit more attractive.

With this construction the diffusion chamber is not mounted on top of the main PCB. This allows the full depth of the instrument 100 to be utilized for the height of the diffusion chamber 105. However, at the same time, the detector 202 must then be separated from the main PCB. As described in more detail below, this allows better shielding of the detector 202, but also means that an electrical connection must be provided between the detector and the rest of the processing on the main PCB.

When the front and rear housing parts 102, 104 are mated together to form an instrument housing, the first chamber part 106 and the second chamber part 108 are brought together in an overlapping relationship such that the second chamber part 108 fits inside the first chamber part 106. The first and second chamber parts 106, 108 mate together in a close-fitting relationship so as to restrict the flow of air through the overlapping region between the two parts. To achieve this overlap, the second chamber part 108 is preferably formed slightly smaller (e.g. with a smaller radius) to fit inside the first part 106. It will be appreciated that in other embodiments the first chamber part 106 may be formed slightly smaller than the second chamber part 108.

Figure 2:
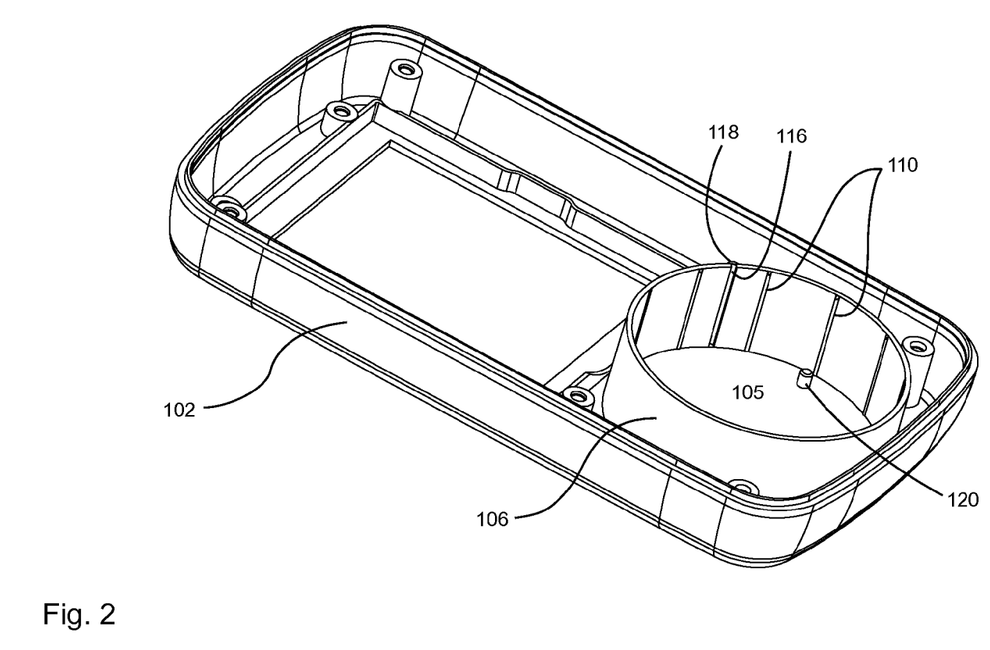
FIG. 2 shows a perspective view of the front housing part of FIG. 1.

The perimeter wall of the first chamber part 106 (i.e. the outer chamber part) has spacer ribs 110 provided on the inner surface thereof so as to maintain a minimum separation between the first and second chamber parts 106, 108 while engaged. Although the first and second chamber parts are close-fitting to restrict gas flow into the chamber 105, these spacer ribs 110 ensure that the chamber 105 is not air tight. The spacer ribs 110 ensure that gas can still diffuse from the outside of chamber 105 to the inside thereof by passing between the overlapped walls of the first and second chamber parts 106, 108. FIG. 2 shows an alternative view of the front housing part, illustrating the spacer ribs 110. It can be seen that each rib 110 is formed with a cross-section in the shape of a circular segment extending inwardly from the inner surface of the wall of chamber part 106. The ribs 110 are elongate in the mating direction of the two chamber parts 106, 108. It will be appreciated that in other embodiments, these spacers need not be formed as ribs, but could be projections of other shapes, so long as they achieve the necessary spaced relationship of the two chamber parts.

In this embodiment, twelve spacer ribs 110 are equally spaced around the perimeter wall of the first chamber part 106, i.e. each rib 110 is separated by 30 degrees from those either side of it. It will be appreciated that twelve is merely an example and the number and spacing of the ribs 110 is not limited to twelve. Rather the number of spacer ribs 110 could be more or less than twelve and the spacing need not be regular. Each rib extends along substantially the entire height of the first chamber part 106 (and therefore substantially the entire height of the chamber 105). The ribs stand proud of the inner surface of the chamber wall by about 0.1 mm (measured in a radial direction, i.e. perpendicular to the chamber wall). Thus the spacer ribs ensure a gap of at least 0.1 mm between the inner surface of the perimeter wall of the outer chamber 106 and the outer surface of the perimeter wall of the inner chamber 108. This gap provides the diffusion path by which gas may enter or leave the diffusion chamber. The maximum size of the gap is determined by the manufacturing tolerances of the instrument housing parts 102, 104. In the embodiment described here for example, the manufacturing tolerance is also about 0.1 mm. Therefore the diffusion path should not exceed 0.2 mm in width (i.e. in the narrowest or most restrictive dimension).

As shown in FIG. 6, a first PCB 200 is disposed inside the diffusion chamber 105. The photodiode 202 which is used to detect alpha particles is mounted on the first PCB 200 and generates an electrical output signal which is conducted outside the diffusion chamber 105 as described in more detail below. First PCB 200 is located within the first chamber part 106. The orientation of first PCB 200 is determined by aligning projections 120 on the inside of first chamber part 106 with locating holes 204 in first PCB 200.

First PCB 200 is dimensioned so that it extends substantially across the whole width of the inside of first chamber part 106. Further, the height of the perimeter wall of the second chamber part 108 is selected such that when the two chamber parts 106, 108 are fully mated together, the rim 109 of the perimeter wall of the second chamber part 108 contacts the first PCB 200 and holds it in position against the end of the first chamber part 106. In other words, the height of the perimeter wall of the second chamber part 108 plus the thickness of the first PCB 200 is equal to the internal separation of the first and second housing parts 102, 104 when mated (at least in the region of the diffusion chamber 105). This arrangement means that the first PCB 200 is securely held in place within the diffusion chamber 105 without the need for any additional fixing means, i.e. there is no need to use adhesive or screws to attach the first PCB 200 to the first housing part 102. This advantageously reduces the number of parts in the instrument as a whole and also reduces the number of steps required to assemble the instrument, thus reducing the assembly time and cost.

As shown in FIGS. 3 and 6, the second chamber part 108 has a number of rim projections 112 which extend from the rim 109 of second chamber part 108 towards PCB 200, i.e.

rim projections 112 extend further from the second housing part 104 than the rest of the perimeter wall of the second chamber part 108. When the two chamber parts 106, 108 are mated together as described above, it is these rim projections 112 which contact the first PCB 200 and hold it in position. The rim projections 112 ensure that the contact between the perimeter wall of the second chamber part 108 and the first PCB 200 do not form an air tight seal. The rim projections 112 ensure that a gap is maintained between the first PCB 200 and the second chamber part 108 so that gas can diffuse between the outside and the inside of the chamber 105. In the embodiment shown here, the rim projections 112 extend 0.1 mm above the rest of the perimeter wall of second chamber part 108, thus leaving a diffusion gap of at least 0.1 mm between the second chamber part 108 and the first PCB 200. The size of this gap is preferably the same as the gap formed by the spacer ribs 110 described above. The rim projections 112 are formed in the same number and with the same spacing as the spacer ribs 110, i.e. twelve rim projections 112 disposed at 30 degree intervals around the perimeter wall. It will be appreciated that other arrangements (e.g. more or fewer projections, regular/irregular spacing) may also be used.

This construction has a number of advantages. The spacer ribs 110 on the wall and the rim projections 112 ensure a minimum separation between the two diffusion chamber parts 106, 108. Together these ensure that the diffusion chamber 105 is not air tight. It is important for the operation of the instrument that radon gas can diffuse into the chamber 105 from outside. At the same time, the first and second chamber parts 106, 108 are formed to be a close fit. In other words, it is desired that the gap between the two chamber parts 106, 108 be close to the minimum separation. The close fitting of the two chamber parts 106, 108 combined with the long overlap of the perimeter walls of the two chamber parts 106, 108 create a diffusion path which significantly impairs diffusion of radon daughter products from outside the chamber 105. There are two factors which impair the diffusion of radon daughter products into the chamber 105. The first is that radon daughter products tend to be charged particles. To pass from the outside to the inside of the chamber 105 such particles have to pass along the very narrow passage formed by the opposing surfaces of the perimeter walls of the first and second chamber parts 106, 108. Charged particles have a tendency to "plate out" on such surfaces and will not progress further along the diffusion path. Therefore there is a low probability that such charged particles will enter the diffusion chamber 105. The second factor is the length of the diffusion path, i.e. the length of overlap between the first and second chamber parts 106, 108. The overlap of the first and second chamber parts 106, 108 is about 15 mm. This length, combined with the narrow width of the diffusion path creates a high time constant for diffusion of gas along the path. The construction described here leads to a time constant of about an hour for diffusion of radon and its daughter products along this path. The combined half lives of the various elements in the radon decay chain from radon-222 through to lead-210 is less than an hour, i.e. less than the time constant of the diffusion path. Therefore even uncharged daughter products of radon-222 have a low probability of traversing the path from outside to inside the chamber 105 before decaying. On the other hand, radon-222 is non-reactive, uncharged and has a half life of 3.8 days so it can readily diffuse into the chamber along this path.

The accuracy of instrument 100 is significantly improved by ensuring that the alpha particles detected by photodiode 202 originate from radon-222 decays within the chamber 105 (i.e. by minimising the quantity of radon daughter products entering the chamber 105 from outside). Detected alpha particles can then all be attributed to a radon decay chain that began inside the well-defined volume of chamber 105 and thus can be used directly to estimate the concentration of radon gas within that volume.

The photodiode 202 is extremely sensitive and so it must be shielded from the electromagnetic noise created by other parts of the instrument, e.g. the signal amplifiers, processing circuitry and LCD display. Therefore to shield the photodiode 202, the diffusion chamber 105 is formed to be electrically conductive. As the chamber parts 106, 108 are formed integrally with the housing parts 102, 104, this is readily achieved either by forming the entire housing parts 102, 104 (including the integrally moulded chamber parts 106,108) of conductive material, e.g. an electrically conductive plastics material, or by coating the interior of the housing parts 102, 104 with a conductive film, e.g. by depositing a conductive film on top of the moulded parts. Thus, when the first and second chamber parts 106, 108 are mated together, they are electrically connected and form a Faraday cage around the photodiode 202, thus shielding it from electromagnetic noise elsewhere in the instrument 100. This Faraday cage is then connected to the ground rail of the rest of the circuitry.

The photodiode 202 does not need to be powered, but the signal it generates upon being struck by an alpha particle needs to be transmitted out of the diffusion chamber 105 to the rest of the processing circuitry for analysis. Thus there must be an electrical connection between the inside and the outside of the diffusion chamber 105. This connection is achieved by means of coaxial cable 206. It will be appreciated that other types of electrical conductor may be used, but a coaxial cable is preferred here in order to maintain the shielding of the signal all the way to the processing circuitry. In addition, the two conductors of the coaxial cable 206 can be used to provide a reverse bias across the photodiode 202. This reverse bias widens the depletion zone which in turn reduces the capacitance of the diode and provides a better signal to noise ratio for the output signal.

As discussed above, the separation between the first and second chamber parts 106, 108 is restricted in order to limit the rate of diffusion between the outside and the inside of the chamber 105. There is therefore not enough room in the gap between those chamber parts 106, 108 for an insulated conductor to pass. In order to allow passage of the coaxial cable 206 from the first PCB 200 on the inside of the chamber 105 to the second PCB 300 on the outside of the chamber 105, a channel 116 is formed in the first chamber part 106. The channel 116 is formed in the inside surface of the perimeter wall of the first chamber part 106 and extends along the wall in the direction from the first housing part 102 to the second housing part 104, i.e. parallel with the spacer ribs 110. The channel 116 closely matches the size and shape of the cable 206 so that when the instrument is assembled, the channel 116 does not provide a substantially easier diffusion path into the chamber 105.

It will be appreciated that channel 116 could be formed in either the inside surface of the first chamber part 106 (as described above), or in the outer surface of the second chamber part 108. However, where the thickness of the perimeter walls of the chamber parts 106, 108 is small, some reinforcement (e.g. extra thickness) 118 may be required in the region of the channel 116. It is better to provide this on the outer chamber part (i.e. first chamber part 106) as this does not then encroach on the volume of the chamber 105.

Figure 1:
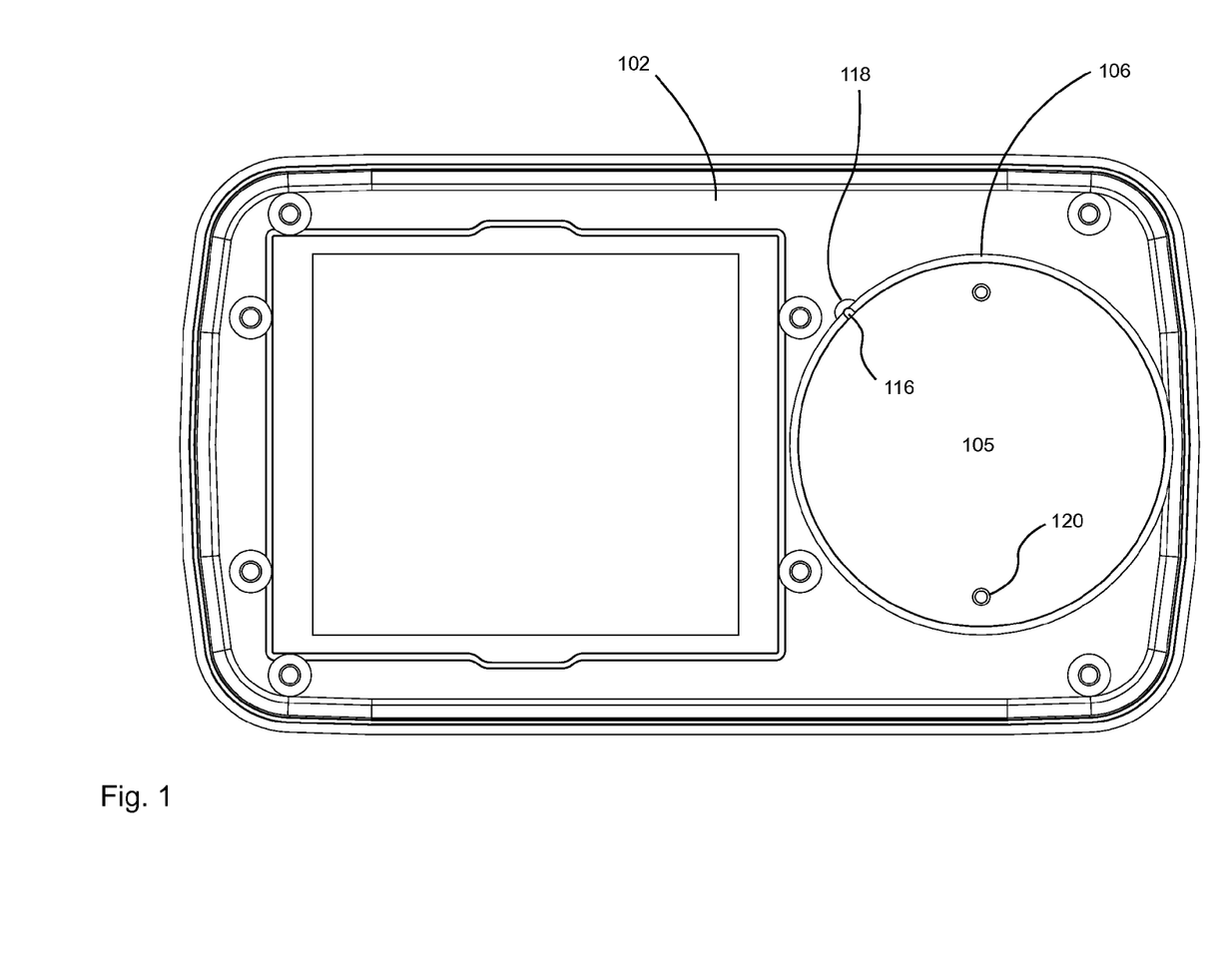
FIG. 1 shows a front housing part of an embodiment of the invention, viewed from the rear.
Figure 4:
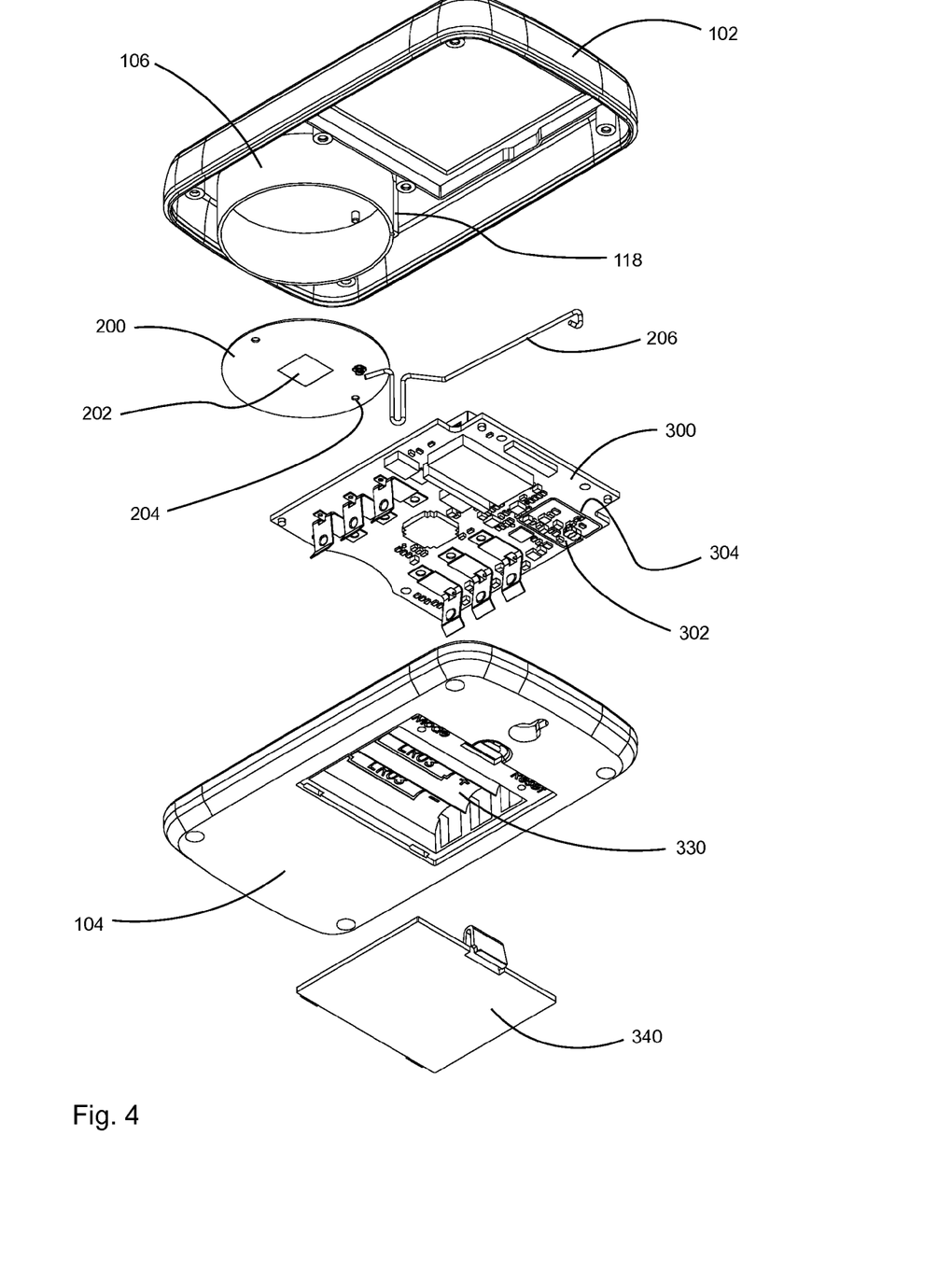
FIG. 4 shows an exploded view of the main components of an embodiment of the invention.

As is shown in FIGS. 1 and 4, reinforcement 118 extends along the outside of first chamber part 106, following the channel 116 on the inner surface thereof.

A notch 114 is formed in the rim 109 of the inner diffusion chamber part 108 so as to provide a passage for coaxial cable 206 to reach channel 116. When the parts 106, 108 are engaged, notch 114 aligns with the base of channel 116.

Amplification and processing of the signal generated by photodiode 202 takes place on second PCB 300 located in the main body of the instrument 100, i.e. between the first and second housing parts 102, 104, but outside the diffusion chamber 105.

The signal received from photodiode 202 is very weak and the first processing step is amplification of that signal. The coaxial cable 206 connects to the second PCB 300 at the input of amplifier circuit 302. At this point the signal is still highly susceptible to electromagnetic interference from other processing circuitry and the LCD display 320. It is therefore necessary to shield the input node and amplifier circuit 302 from the remaining circuitry in order to increase the accuracy of the instrument 100. In particular, this is important for measuring the amplitude of the signal and thus the energy of the alpha particles emitted by radon and its daughters, this being important to decide the origin of the alpha particle from either Radon-222 or its daughters.

To achieve such shielding, a Faraday cage is formed around these components. The bottom of the Faraday shield is formed from the underside 301 of PCB 300. PCB 300 is a dual layer circuit board with the majority of the components and tracks mounted on one side 303, thus leaving the second side 301 as a uniform conductor. Mounting all the components on one side has the advantage of simplifying the assembly process, while using a dual layer PCB 300 with the second layer 301 unused provides the bottom of the Faraday shield around the input node and amplification circuit 302. An LCD display 320 for the instrument 100 may be mounted on the second layer 301, although in other embodiments it could be mounted on the same side as the rest of the components.

Figure 7A:
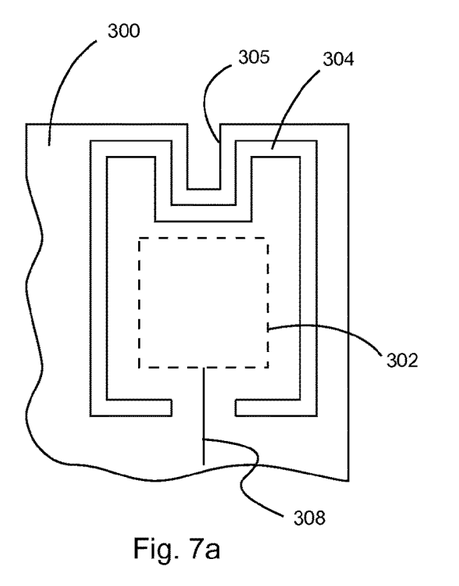
FIGS. 7a and 7b show alternative embodiments of a PCB with an input amplifier circuit.

On the component side 303 of second PCB 300, the input node and amplification circuit 302 are substantially surrounded by a conductive track 304. Conductive track 304 is broken (interrupted) at one place 306 in order to provide an exit for the output tracks 308 of the amplifier circuit 302. In other words, conductive track 304 forms a C-shape around the amplification circuit 302, as shown in FIG. 7a.

The conductive track 304 is merely an exposed contact portion of the first conductive layer 303. In the formation process of the PCB, portions of the conductive layer 303 are etched off to leave conductive tracks electrically linking the various components of the circuit. The remaining unused portions of conductive layer 303 are connected to the circuit ground. The amplifier circuit 302 is surrounded by such unused portions of conductive layer 303.

To protect the conductive tracks which have been formed in the PCB by the etching process, the PCB is typically covered with a protective insulating solder stop layer. This layer protects the underlying tracks from undesired short-circuits. However the portions of the conductive layer 303 where components are to be mounted must be left open for making electrically connections, i.e. they are not covered by the solder stop, thus leaving contact pads where the components can be soldered. Conductive track 304 is also formed in this way, i.e. conductive track 304 is free from solder stop and forms a contact pad for external connection to the unused copper layer 303. Conductive track 304 is thus formed in a shape substantially corresponding to the shape of the rim of tubular enclosure 312.

The signal enters the amplifier circuit from mini-coax cable 206. A slit 305 is formed in the side of the second PCB 300 to allow the cable 206 to enter the Faraday cage from the other side of the PCB 300. As shown in FIG. 7a, the conductive track 304 follows the contour of this slit 305, but in an alternative embodiment, the track 304 could also be interrupted here, thus dividing the track 304 into two parts. The enclosure 312 is of a simple rectangular cross-section so that the rim of the enclosure 312 simply passes straight across slit 305, unlike track 304. Thus the coaxial cable 206 passes up into the inside of the Faraday cage.

Figure 7B:
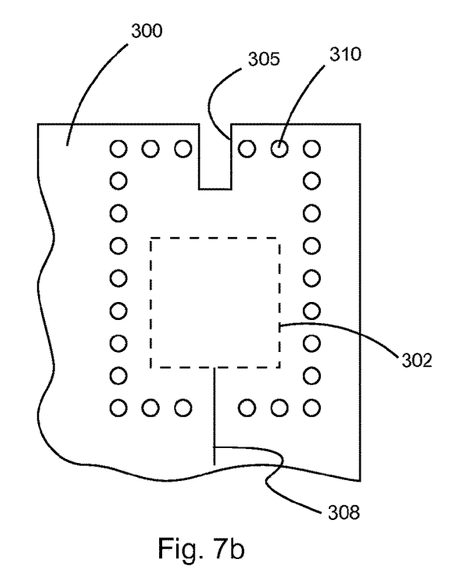

In an alternative embodiment illustrated in FIG. 7b, there is no conductive track 304 formed in the first conductive layer 303, but merely the conductive tops of the vias 310 which electrically connect the rim of enclosure 312 with the second conductive layer 301. It can be seen that the boundary around circuit 302 which is formed by the vias 310 is in the shape of two opposed square brackets ([ ]) with a break at one end for the exit track 308 of the amplifier circuit 302, and a break at the opposite end for the slit 305 where coaxial cable 206 enters the Faraday cage. Again the enclosure 312 passes straight across the slit 305.

In yet another embodiment which is not illustrated, but is similar to FIG. 7b, the vias 310 do not pass along a line which intersects the slit 305, but pass along an uninterrupted straight line, perpendicular to the slit 305 and passing between the end of the slit 305 and the circuit 302.

Figure 8:
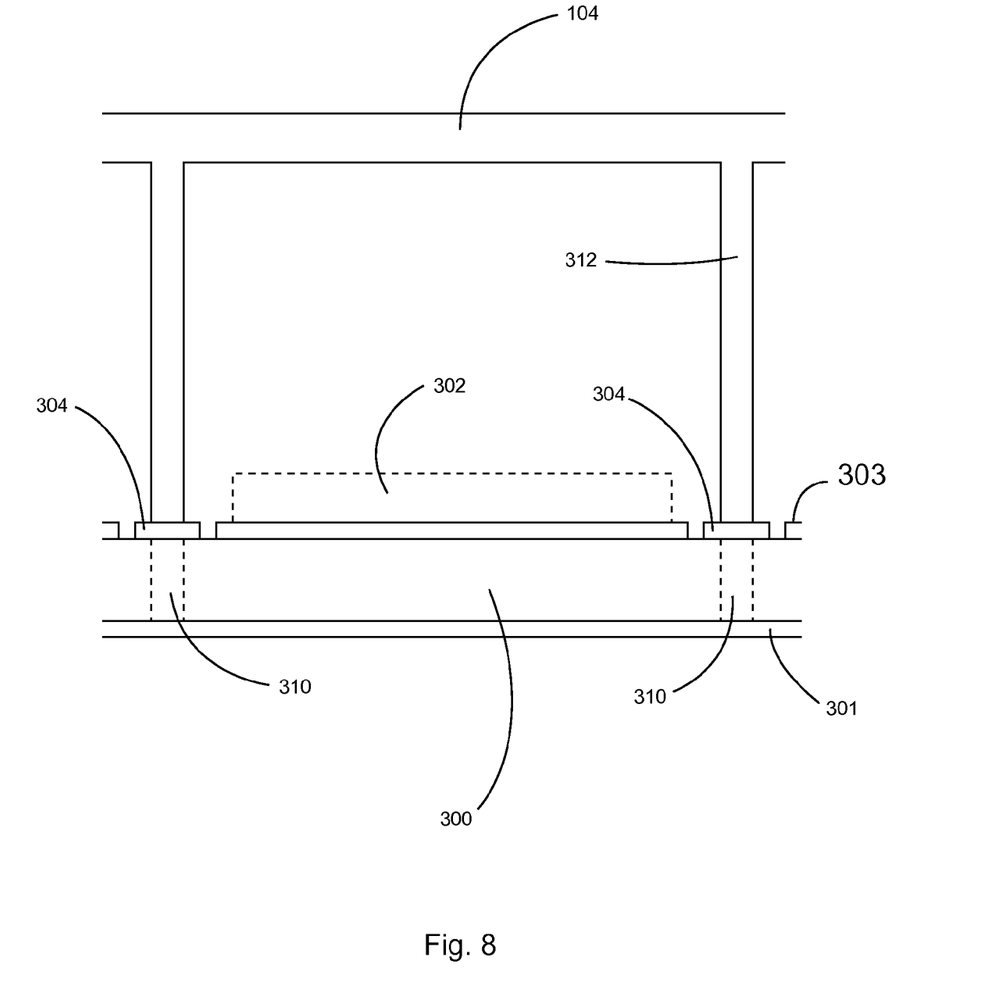
FIG. 8 shows a cross-sectional view of a Faraday cage for the input node in an assembled instrument.
Figure 9:
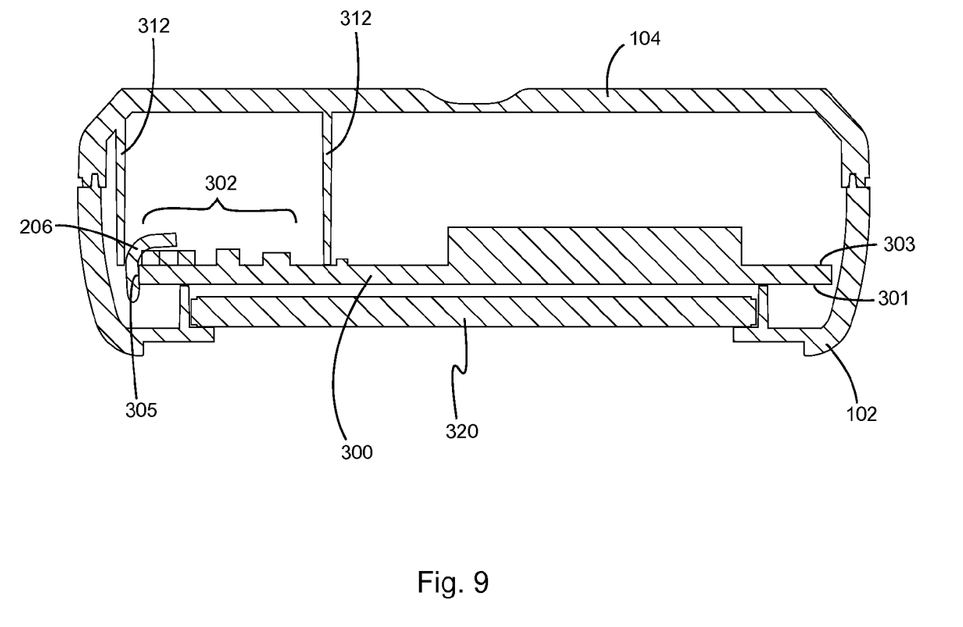
FIG. 9 shows a cross-sectional view of an instrument with an integral Faraday cage.

FIG. 8 illustrates a cross-section through the Faraday cage and the second PCB 300. FIG. 9 shows a similar cross-sectional view taken through the instrument 100 as a whole and showing the coaxial cable 206 entering the Faraday cage via slit 305.

Conductive track 304 is connected to the underside 301 of second PCB 300 by a plurality of vias 310, being holes passing through the second PCB 300 from the conductive track 304 to the underside 301 and filled with conductive material. Vias 310 are formed at regular intervals around track 304 in order to maintain the electrical connection of the Faraday shield around the input node and amplifier circuit 302. To complete the Faraday cage, a conductive shielding enclosure 312 is pressed against the conductive track 304 to surround the input node and amplifier circuit 302 from above. The shielding enclosure 312 is formed integrally with the second housing part 104 (i.e. the back housing part with the battery compartment 330). As mentioned above, the second housing part 104 is formed from a conductive material such as conductive plastics or metallised plastics (e.g. with a metal film on its inner surface). Thus the shielding enclosure 312 is advantageously formed as part of the moulding and/or coating process of the instrument housing part 104. This reduces cost and simplifies assembly as a separate component is not required to complete the Faraday cage around the input node and amplifier 302. Instead, the Faraday cage is simply completed when the two housing parts 102, 104 are mated together, thus forcing the integral shielding enclosure 312 into contact with the conductive track 304 on the second PCB 300. It will be appreciated that in other embodiments, the enclosure 312 could be formed on the first housing part 102 so long as in use it faces the input node where the detector signal feeds into the main PCB 300 and the amplifier circuit 302.

When the enclosure 312 is in position over the amplifier circuit 302, the wall of the enclosure 312 extends straight across the slit 305 in second PCB 300, thus enclosing the end of coax cable 206 within the Faraday cage.

As described above, a break 306 in conductive track 304 allows exit tracks 308 to conduct the output signal of amplifier circuit 302 out of the Faraday cage and on to the rest of the processing circuitry. As the shielding enclosure 312 is electrically conductive and is pressed down onto second PCB 300, it is necessary to protect the exit tracks 308 from contact with the shielding enclosure 312. The tracks 308 can be protected to a certain extent by an insulating layer of solder stop applied over the tracks 308, but when the housing parts 102, 104 are connected together during assembly, the shielding enclosure 312 is pressed against the second PCB 300. If the pressure applied between these components is too great, the solder stop may be damaged and short-circuiting of the exit tracks 308 may occur. Damage may of course occur in other ways too. Therefore to prevent short-circuiting, a recess 314 (see FIG. 3) is provided in the perimeter wall of the shielding enclosure 312 so that when it is pressed against second PCB 300, the recess 314 does not make contact with the second PCB 300, thus avoiding the potential short-circuiting problem. Recess 314 must of course be small enough that it does not adversely affect the functioning of the Faraday cage. In the embodiment described here, the recess has a height of 0.3 mm, i.e. it provides a 0.3 mm gap above the exit tracks 308. In other embodiments the recess may have a height of between 0.1 mm and 0.5 mm, although the acceptable dimensions will depend on the frequencies which are to be blocked.

With the use of conductive plastics or metallized plastics for the instrument housing parts 102, 104 as described above, the instrument housing as a whole provides a first level of electromagnetic shielding that excludes interference from sources external to the instrument. Within the housing, the integral diffusion chamber parts 106, 108 provide a Faraday cage around the diffusion chamber and the photodiode 202 and the integral shielding enclosure 312 provides a Faraday cage around the input signal and the amplifier circuit 302. All of this shielding is achieved in the same assembly step of mating the two instrument housing parts 102, 104 together.

The assembly of the instrument 100 will now be described with reference to FIG. 4 which shows an exploded view of the various components. The housing parts 102, 104 are initially separate. First the LCD display 320 is installed in the front housing part 102 and zebra strip connectors (not shown) are placed thereon to provide electrical connection to the second PCB 300 (it should be noted that, for clarity, the LCD display 320 is shown just behind the PCB 300 and is only just visible in FIG. 4). The mini coax cable 206 is connected to second PCB 300 and the second PCB 300 is then fixed to the front housing 102, thus making electrical contact between the LCD display 320 and the contacts on the underside 301 of second PCB 300. First PCB 200 is then placed inside the first diffusion chamber part 106 so that the locating holes 204 engage with locating pins 120. The other end of mini coax cable 206 is connected to first PCB 200 and is seated in the channel 116 in the side of the first diffusion chamber part 106. The back housing part 104 is then connected to the front housing part 102. In addition to completing the housing of the instrument, this last assembly step mates the two diffusion chamber parts 106, 108 and also brings the enclosure 312 into contact with the conductive track 304 on second PCB 300. As the front and rear housing parts 102, 104 are conductive (in this embodiment they have been coated with a thin metal layer by vacuum metallization), this assembly step electrically connects the two housing parts 102, 104, including the two diffusion chamber parts 106, 108, and electrically connects the enclosure 312 with the conductive track 304, thus forming a Faraday cage around the amplifier circuit 302 on the second PCB 300. Finally, the step of mating the two housing parts 102, 104 also secures first PCB 200 in position within first diffusion chamber part 106 as second diffusion chamber part 108 impinges thereon.

The attachment of the second PCB 300 to the housing may be made in any suitable way. However, in this embodiment it is preferred to use conductive screws. As the front housing part 102 is electrically conductive, the conductive screws can advantageously be used to connect the housing parts 102, 104 (and thereby also the diffusion chamber parts 106, 108 and enclosure 312) to the ground rail of the electronics.

Similarly, the front and rear housing parts 102, 104 may be fixed together in any suitable way, e.g. via clips, hooks or screws.

The instrument 100 described here is a low power instrument which runs on standard commercially available batteries, e.g. AA or AAA size batteries. Due to its compact size and non-reliance on external power, the instrument can be deployed in a wide range of locations, e.g. in small cavities or in places where grid power is not available.

Rear housing 104 contains a battery compartment 330 for housing the batteries, which, in use, are covered by a battery lid 340.

It should be noted that, for clarity, no spacer ribs 110 are shown in FIGS. 1 and 4

Figure 5A:
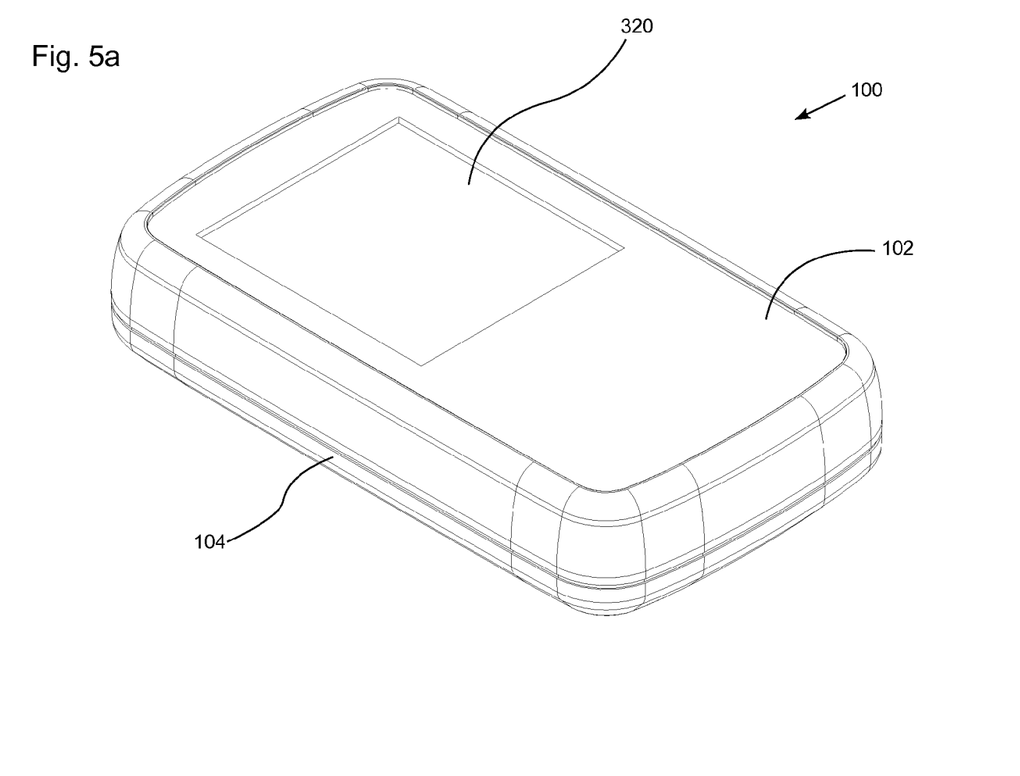
FIGS. 5a and 5b show a fully assembled instrument.
Figure 5B:
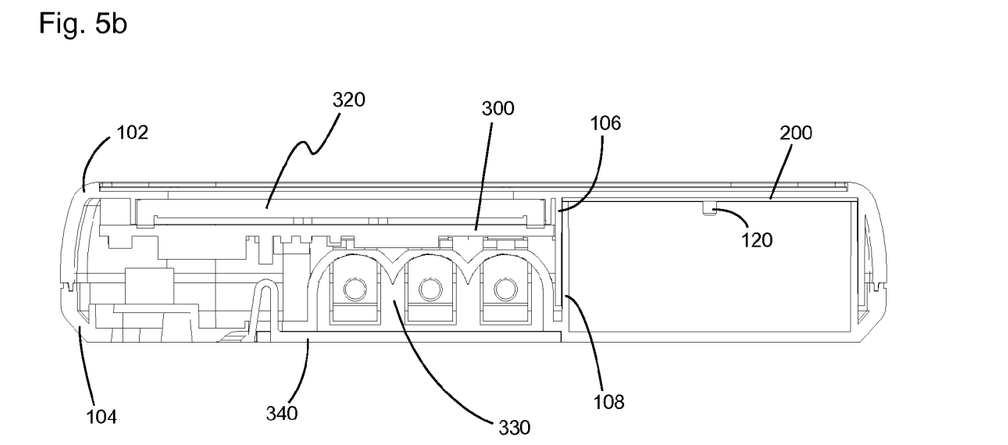

The fully assembled instrument 100 is shown in FIGS. 5a and 5b (cross-section).

It will be appreciated that the above description is of a radon gas sensor. However the principles embodied in that description apply equally well to other gas sensors with a diffusion chamber. The size of the diffusion chamber and the width and length of the diffusion path created by the overlap can readily be varied according to the gas or gases in question so as to allow passage of selected gases or particles while hindering passage of other gases or particles. An appropriate detector for placement inside the diffusion chamber can also be selected for monitoring the concentration of the particular gas or gases in question.

It will also be appreciated that, although the above description specifies a photodiode for detecting alpha particles, other radiation detectors can also be used so long as the measurements can be correlated to the concentration of radon within the diffusion chamber.

The invention claimed is:

1. An instrument comprising:
   a housing including a housing part having an inner surface; and
   a printed circuit board disposed within the housing;
   wherein the housing part of the instrument comprises an integral tubular projection extending from the inner surface thereof towards the printed circuit board so as to surround at least one electronic component thereon;
   wherein the inner surface and a rim of said integral tubular projection are electrically conductive so that the tubular projection forms part of a Faraday cage around said at least one component;
   wherein the tubular projection includes a recess in the rim thereof which does not make contact with the printed circuit board;
   wherein the printed circuit board comprises at least first and second conductive layers, the second conductive layer being located further from the tubular projection than the first conductive layer, wherein the at least one component is mounted on the first conductive layer, and wherein a plurality of electrically conductive vias through the printed circuit board electrically connect the rim of the tubular projection with the second conductive layer;

wherein the plurality of electrically conductive vias are positioned along a boundary which substantially surrounds the component; and wherein said boundary and said plurality of electrically conductive vias deviate from the rim of said integral tubular projection in a region where a signal cable enters the Faraday cage.

2. The instrument as claimed in claim 1, wherein the one or more vias electrically connect one or more portions of the first layer with the second layer.

3. The instrument as claimed in claim 1, wherein the second layer is substantially continuous across the area defined by the rim of the tubular projection.

4. The instrument as claimed in claim 1, wherein the integral tubular projection surrounds a plurality of components, including the at least one component, forming a circuit.

5. The instrument of claim 4, wherein the circuit is an amplifier circuit.

6. The instrument as claimed in claim 1, wherein a whole inside surface of the instrument housing is conductive.

7. The instrument as claimed in claim 1, wherein the instrument is a radon gas sensor.

* * * * *